United States Patent
Estabrook

[19]

[11] Patent Number: 5,935,144
[45] Date of Patent: Aug. 10, 1999

[54] DOUBLE SEALED ACOUSTIC ISOLATION MEMBERS FOR ULTRASONIC

[75] Inventor: Brian Estabrook, Foxboro, Mass.

[73] Assignee: Ethicon Endo-Surgery, Inc., Cincinnati, Ohio

[21] Appl. No.: 09/058,088

[22] Filed: Apr. 9, 1998

[51] Int. Cl.$^6$ .................................................. O61B 17/32
[52] U.S. Cl. .................. 606/169; 606/167; 606/168; 606/170; 604/22; 604/24
[58] Field of Search .................. 606/169, 167, 606/168, 170–174, 176–184, 79–85; 604/22, 24

[56] References Cited

U.S. PATENT DOCUMENTS

| | | | |
|---|---|---|---|
| 2,990,616 | 7/1961 | Balamuath et al. | 32/26 |
| 3,053,124 | 9/1962 | Balamuth et al. | 78/82 |
| 4,492,574 | 1/1985 | Warrin et al. | 433/81 |
| 4,634,420 | 1/1987 | Spinosa et al. | 604/22 |
| 5,038,756 | 8/1991 | Kepley | 128/24 AA |
| 5,058,570 | 10/1991 | Idemoto et al. | 128/24 AA |
| 5,322,055 | 6/1994 | Davison et al. | 601/2 |
| 5,449,370 | 9/1995 | Vaitekunas | 606/169 |
| 5,505,693 | 4/1996 | Mackool | 604/22 |
| 5,678,551 | 10/1997 | Stevens | 128/660.01 |

*Primary Examiner*—Michael Buiz
*Assistant Examiner*—Lien Ngo
*Attorney, Agent, or Firm*—Bernard Shay

[57] ABSTRACT

An ultrasonic surgical instrument is described for use in medical procedures to, for example, dissect or cut living organic tissue. The ultrasonic surgical instrument includes an outer sheath, a waveguide, and an improved acoustic isolation element. The acoustic isolation element is bonded to both the ultrasonic waveguide and the interior surface of the outer sheath, creating an acoustic isolation seal. The improved acoustic isolation element seals the distal end of the ultrasonic instrument, substantially improving its ability to reduce or eliminate penetration by liquids or other contaminants during, for example, soaking or steam autoclave sterilization.

12 Claims, 5 Drawing Sheets

DOUBLE SEALED ACOUSTIC ISOLATION MEMBERS FOR ULTRASONIC

This application is related to the following copending applications, which are hereby incorporated herein by reference: U.S. patent application Ser. Nos. 08/808,273, filed Feb. 28, 1997 [Attorney Docket No.END-394]; 08/808,652, filed Feb. 28, 1997 [Attorney Docket No.END-395]; and 08/949,161, filed Oct. 10, 1997 [Attorney Docket No.END-470].

FIELD OF THE INVENTION

The present invention relates, in general, to an improved acoustic isolation element for use in an ultrasonic surgical instrument and, more particularly, to an acoustic isolation element which includes a sealing material adapted to seal the acoustic isolation element to an outer acoustic isolation tube.

BACKGROUND OF THE INVENTION

Ultrasonic surgical instruments may be used in medical procedures to, for example, dissect or cut living organic tissue. The dissecting or cutting action is accomplished by a surgical end-effector, such as a hook, at the distal end of the ultrasonic instrument. In an ultrasonic instrument, the end-effector cuts by transmitting ultrasonic energy to the tissue. Ultrasonic energy may also be used to arrest or minimize bleeding in tissue surrounding the surgical end-effector, causing hemostasis by coagulating blood or sealing vessels in the surrounding tissue.

Ultrasonic vibration is induced in the surgical end-effector by, for example, electrically exciting a transducer which may be constructed of one or more piezoelectric or magnetostrictive elements in the instrument handpiece. Vibrations generated by the transducer section are transmitted to the surgical end-effector via an ultrasonic waveguide which extends from the transducer section to the surgical end-effector.

In prior ultrasonic instruments, the waveguide of the instrument, through which ultrasonic energy is directed, is typically provided with one or more acoustic isolation elements which may be, for example, O-rings or other ring-like members. The acoustic isolation elements, which are positioned at vibratory nodes, acoustically damp the waveguide, thus preventing or reducing annoying or unwanted sounds. In addition, where the ultrasonic instrument includes an outer sheath, the acoustic isolation elements isolate the waveguide from the outer sheath. Such acoustic isolation elements are typically provided at one or more nodes of longitudinal vibration of the waveguide and are typically constructed of elastomeric material, such as silicone rubber. Acoustic isolation elements of this type are adapted to prevent loss of vibrational energy from the waveguide which can occur when the waveguide comes in contact with the outer sheath. Such contact can occur under side-loading or bending conditions, such as when force is applied to the surgical end-effector.

Acoustic isolation elements consisting of rubber O-rings are described in U.S. Pat. No. 5,449,370. Also described in U.S. Pat. No. 5,449,370 is the use of a polymeric sheath comprising protrusions formed of the polymeric material in contact with a waveguide, where the protrusions act as an acoustic isolation element between the waveguide and the sheath. U.S. Pat. No. 5,322,055 describes the use of acoustic isolation mounts positioned at nodes of ultrasonic vibration to avoid dampening or dissipation of desired energy transmission from a transducer to an end-effector. The acoustic isolation mounts described in U.S. Pat. No. 5,322,055 are not bonded to the outer sheath, facilitating the disassembly of the ultrasonic surgical instrument for subsequent cleaning.

Ultrasonic surgical instruments have been described which incorporate an acoustic isolating element which is also adapted to provide a seal. Such an arrangement is disclosed in U.S. patent application Ser. No. No. 08/949,161, filed Oct. 10, 1997, which was previously incorporated herein by reference. The device described in Ser. No. 08/949,161 includes an acoustic isolation element sealed to an acoustic waveguide, and in direct contact with an outer sheath or tube member, wherein the acoustic isolation element is positioned at the waveguide node closest to the distal end of the outer sheath.

Previously, acoustic isolation elements and acoustic isolation seals have been added to ultrasonic waveguides by, for example, injection molding silicone rubber onto the acoustic waveguides at vibratory nodes. Adhesion of the acoustic isolation element to the waveguide has been improved by the use of a primer material between the acoustic isolation element and the waveguide. When an outer sheath is positioned around a waveguide which includes an acoustic isolation seal, the acoustic isolation seal is compressed between the outer surface of the waveguide and the inner surface of the outer sheath. The compression fit of the acoustic isolation seal between the waveguide and the outer sheath creates a compression seal which is generally impervious to liquids or gasses when the instrument being used. However, such seals may allow liquid or steam to pass when the instrument is being sterilized by, for example, soaking or steam autoclaving. While this is generally not a problem for disposable instruments or instruments which can be disassembled before sterilizing, it may be a disadvantage in reusable instruments, particularly where the instrument cannot be disassembled prior to sterilization or where it would not be advantageous to disassemble the instrument before sterilization. Thus, during steam autoclave sterilization small amounts of steam may pass through the compression seal. Preventing fluids and steam from entering the space between the ultrasonic waveguide and the outer sheath is believed to enhance the useful life of reusable ultrasonic instruments.

It would, therefore, be advantageous to design an improved acoustic isolation seal which is substantially impervious to fluids and gasses, even during sterilization of the instrument. It would further be advantageous to form the acoustic isolation seal of a material which does not pass steam during sterilization. It would further be advantageous to provide an acoustic isolation seal which is substantially impervious to soaking or steam autoclave sterilization, thus sealing the instrument and preventing liquids or other contaminants from entering into the interior of the instrument. Furthermore, it would be advantageous to provide an acoustic isolation seal which is bonded to both the outer surface of the waveguide and the inner surface of the outer sheath of an ultrasonic surgical device, reducing the need for compression of the seal. Such an improved acoustic isolation seal would be particularly suited for use in reusable instruments such as those which are adapted for multiple patient use and are subjected to multiple sterilization cycles.

SUMMARY OF THE INVENTION

An ultrasonic surgical instrument comprising an outer sheath having a proximal end, a distal end, and an inner surface. An ultrasonic waveguide is positioned within the outer sheath and has an end-effector extending from the distal end of the outer sheath. The instrument contains an acoustic isolation seal wherein the acoustic isolation seal is bonded to both the ultrasonic waveguide and the outer sheath interior surface.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
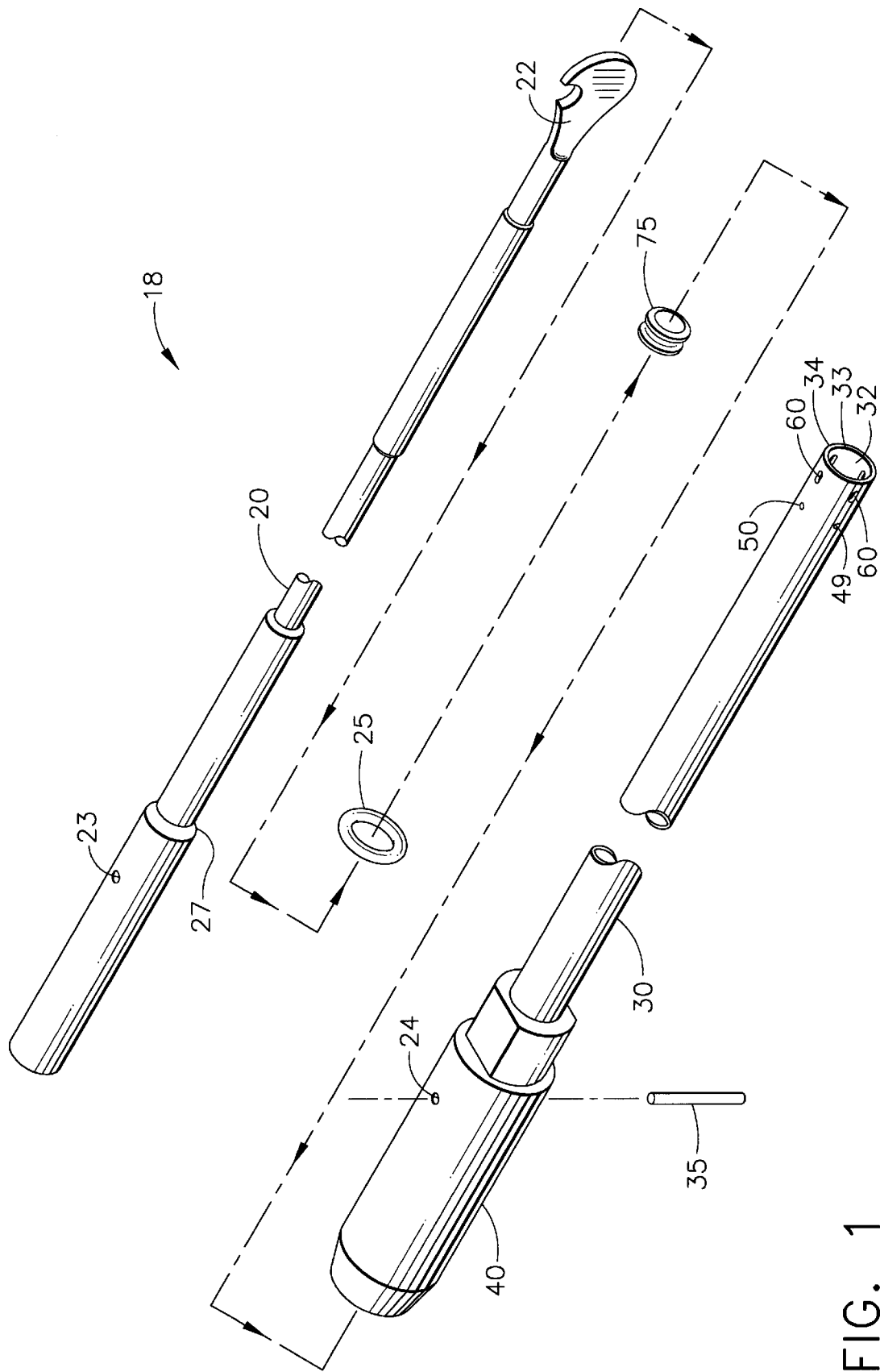
FIG. 1 is an exploded perspective view illustrating an ultrasonic instrument according to the present invention, including an ultrasonic waveguide, outer sheath and hook blade end-effector.

FIG. 1 is an exploded perspective view illustrating an ultrasonic instrument 18 according to the present invention, including an ultrasonic waveguide 20, outer sheath 30 and hook blade end-effector 22. When ultrasonic instrument 18 is assembled, ultrasonic wave guide 20 is positioned in outer sheath 30 with hook blade end-effector 22 projecting from opening 33 in distal end 34 of outer sheath 30. Ultrasonic waveguide 20 is affixed to outer sheath 30 by connector pin 35 which is positioned in sheath pin hole 24 and waveguide pin hole 23. O-ring 25 and acoustic isolation element 75 support waveguide 20 within outer sheath 30.

Figure 2:
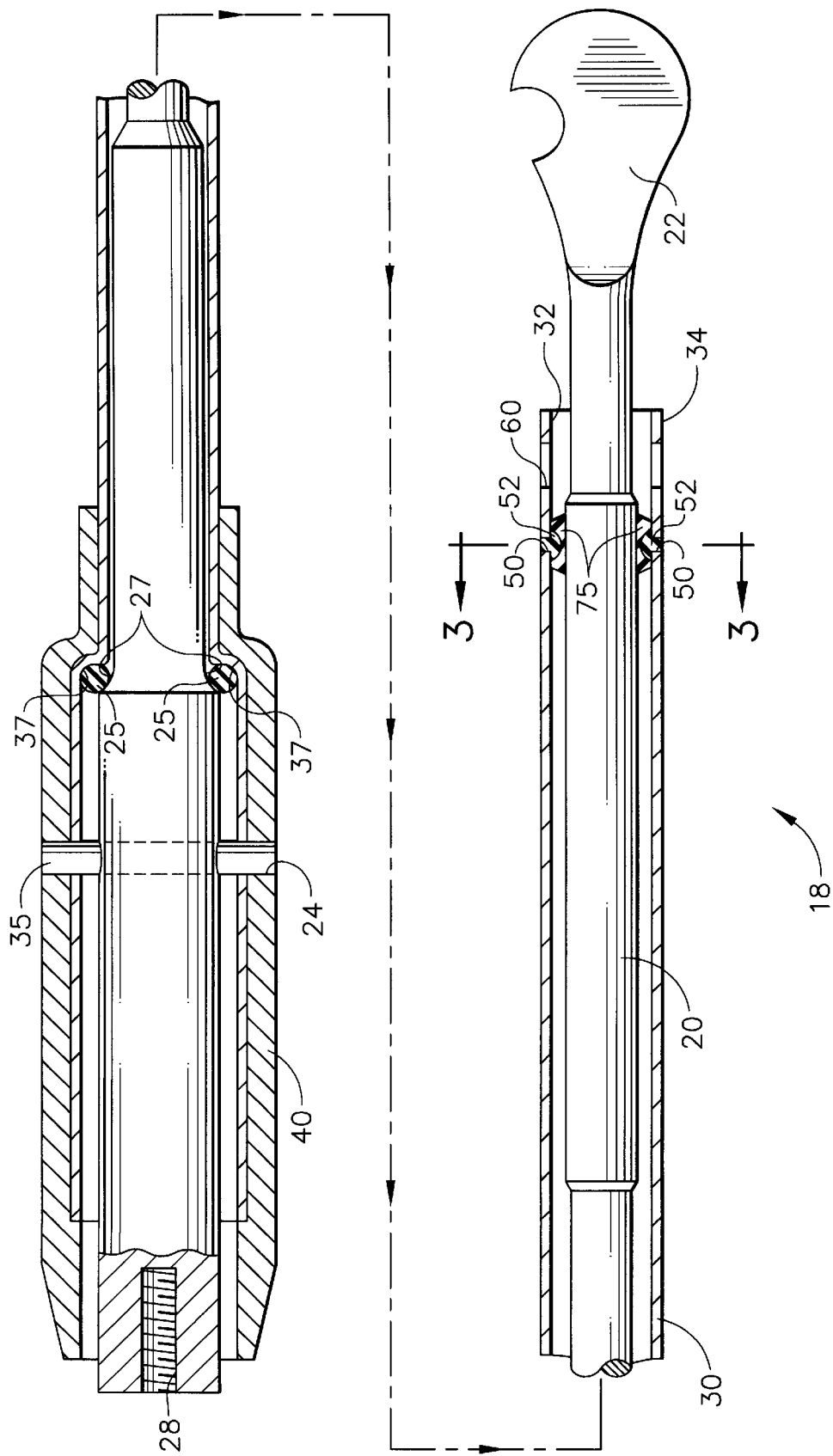
FIG. 2 is a cutaway side view of the ultrasonic instrument illustrated in FIG. 1.

FIG. 2 is a cutaway side view of ultrasonic instrument 18. In FIG. 2, O-ring 25 is positioned between outer sheath mounting shoulder 37 and waveguide shoulder 27 to position the proximal end of ultrasonic waveguide 20 in outer sheath 30. Acoustic isolation element 75 is most advantageously positioned at the distal-most vibratory node of waveguide 20. Acoustic isolation element 75 is fixed to wave guide 20 by, for example, molding seal 75 onto waveguide 20 utilizing an injection molding process. Acoustic isolation element 75 is bonded to outer sheath 30 by, for example, injecting sealant 52 into the region between acoustic isolation element 75 and inner surface 32 of outer sheath 30. Injector holes 49 (shown in FIG. 3) and 50 are positioned to provide access through outer sheath 30. Attachment threads 28 are positioned at the proximal end of ultrasonic instrument 18 to facilitate attachment of instrument 18 to an ultrasonic handpiece (not shown) such as the ultrasonic handpiece shown and described in application Ser. No. 08/808,273, filed Feb. 28, 1997, which was previously incorporated herein by reference. In order to more clearly illustrate the interface between acoustic isolation element 75 and outer sheath 30, embodiments of the seal region of instrument 18 in FIG. 2 are shown in magnified form in FIGS. 3, 6, and 7.

Figure 3:
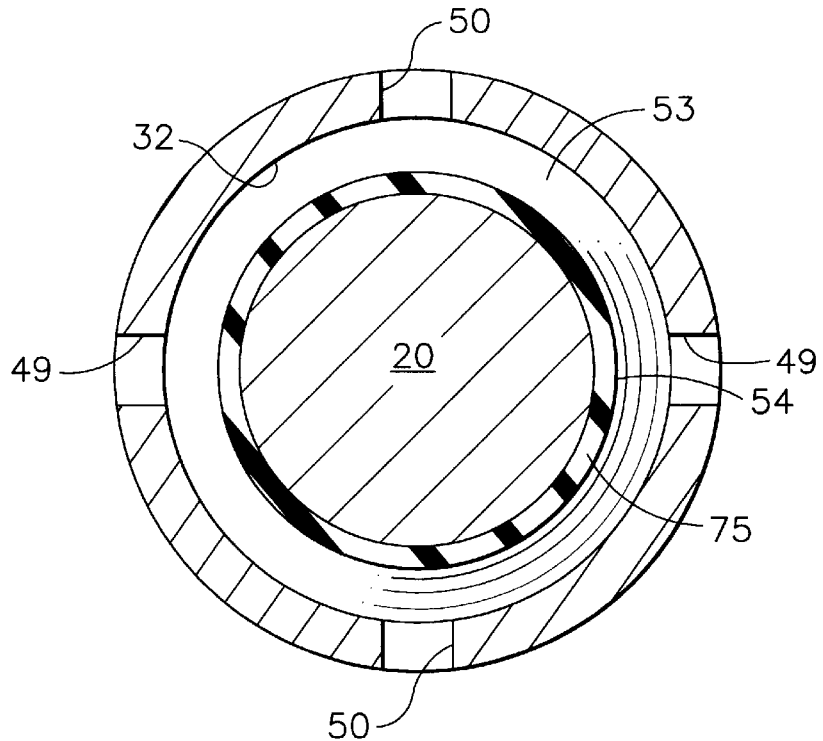
FIG. 3 is a magnified cross-sectional view of the seal region of the distal end of the ultrasonic instrument illustrated in FIG. 2. The sealant shown in FIG. 2 has been removed from the FIG. 3 view for clarity.

FIG. 3 is a magnified cross-sectional view of the seal region at the distal end of ultrasonic instrument 18, with sealant 52 removed from the view for clarity. In FIG. 3, acoustic isolation element 75, which is positioned between waveguide 20 and outer sheath 30, defines a annular recess 53. Annular recess 53 is accessible through first injection opening 49 and second injection opening 50. Acoustic isolation element 75 is formed from an elastomeric material, such as, for example, silicone rubber, or VITON® a trademark name for a fluoroelastomer synthetic rubber material that is manufactured by DuPont. The region between annular groove 54 and inner surface 32 of outer sheath 30 defines annular recess 53. Sealant 52 (not shown in this figure) fills annular recess 53. Sealant 52 may be injected by, for example, forcing sealant 52 through a first injection opening 49, replacing air which is forced out of a second injection opening 50.

Figure 4:
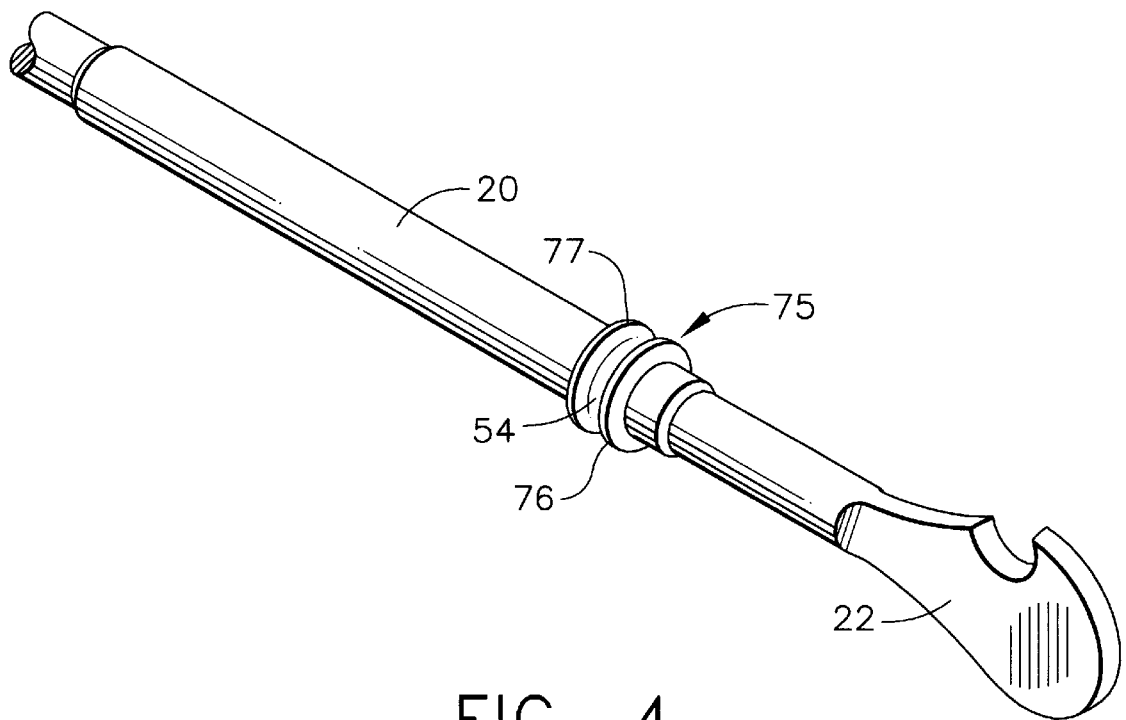
FIG. 4 is a fragmentary, perspective view of the distal end of an ultrasonic waveguide including an acoustic isolation element and a hook blade end-effector.

FIG. 4 is a fragmentary, perspective view of the distal end of ultrasonic waveguide 20 including acoustic isolation element 75 and hook blade end-effector 22, with outer sheath 30 removed. Acoustic isolation element 75 is positioned near the distal most node of acoustic longitudinal vibration of ultrasonic waveguide 20. Annular groove 54 is located between distal sealing ridge 76 and proximal sealing ridge 77.

Figure 5:
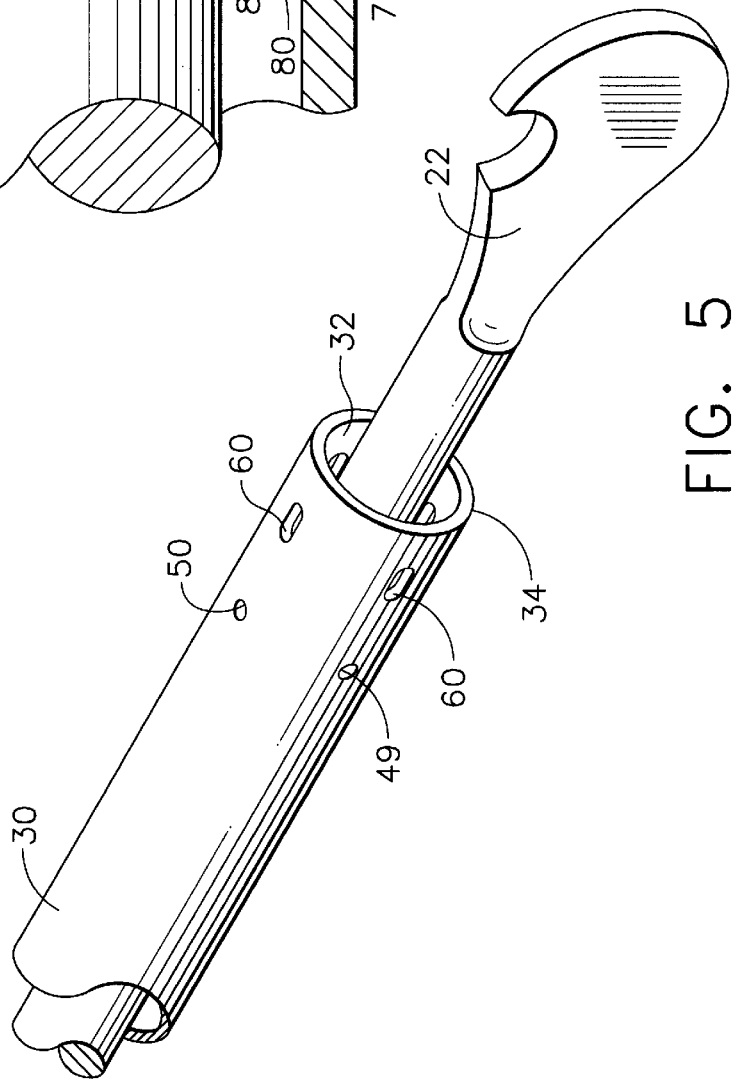
FIG. 5 is a magnified perspective view of the distal end of the instrument illustrated in FIG. 2.

FIG. 5 is a perspective view of distal end of ultrasonic instrument 18. In FIG. 5, cleaning ports 60 are positioned in outer sheath 30, distal to acoustic isolation element 75 and injection opening 50, and proximal to distal end 34 of outer sheath 30. Cleaning ports 60 are elongated and extend through outer sheath 30 to facilitate cleaning of the space between inner wall 32 and waveguide 20 distal to acoustic isolation element 75.

Figure 6:
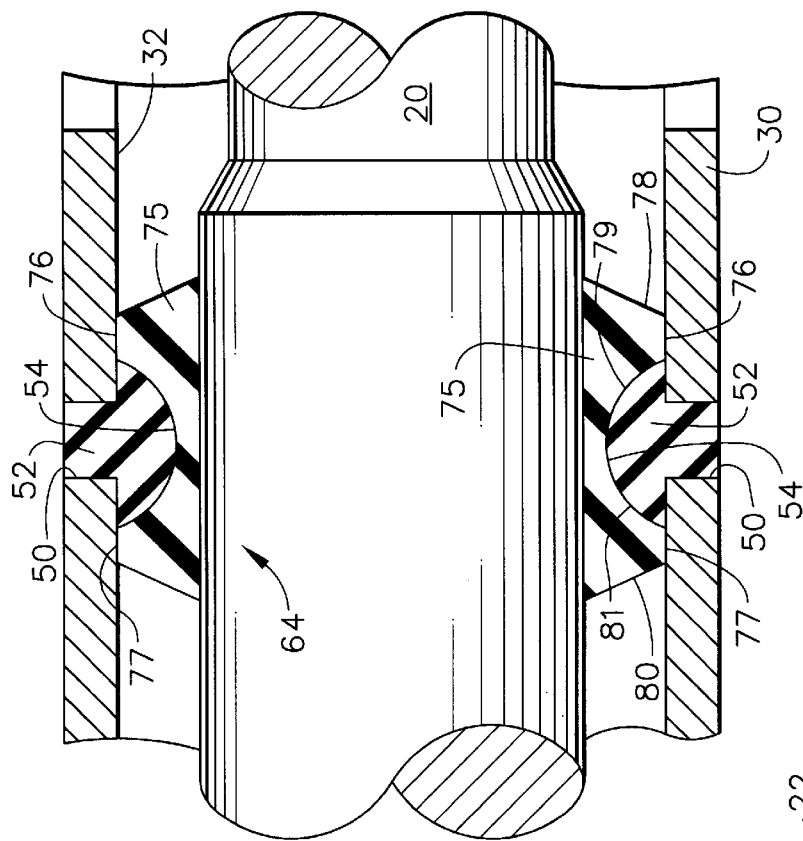
FIG. 6 is a magnified cutaway view of the seal region of the distal end of the ultrasonic instrument illustrated in FIG. 2.

FIG. 6 is a magnified cutaway view of the seal region of the distal end of ultrasonic instrument 18. In FIG. 6, acoustic isolation element 75, is positioned between waveguide 20 and outer sheath 30. Annular recess 53 is accessible through first injection opening 49 (shown in FIG. 3) and second injection opening 50. Acoustic isolation element 75 includes distal sealing ridge 76, proximal sealing ridge 77 and annular groove 54. The region between annular groove 54 and inner surface 32 of outer sheath 30 defines annular recess 53. Sealant 52 fills annular recess 53.

As illustrated in FIG. 6, distal sealing ridge 76 is formed by first distal converging surface 78 and second distal converging surface 79 which may be, for example, generally frusto-conical in shape. First distal converging surface 78 and second distal converging surface 79 converge to define a thin and compliant peripheral sealing ridge 76. Proximal sealing ridge 77 is formed by first proximal converging surface 80 and second proximal converging surface 81 which may be, for example, generally frusto-conical in shape. First proximal converging surface 80 and second proximal converging surface 81 converge to define a thin and compliant peripheral sealing ridge 77.

Figure 7:
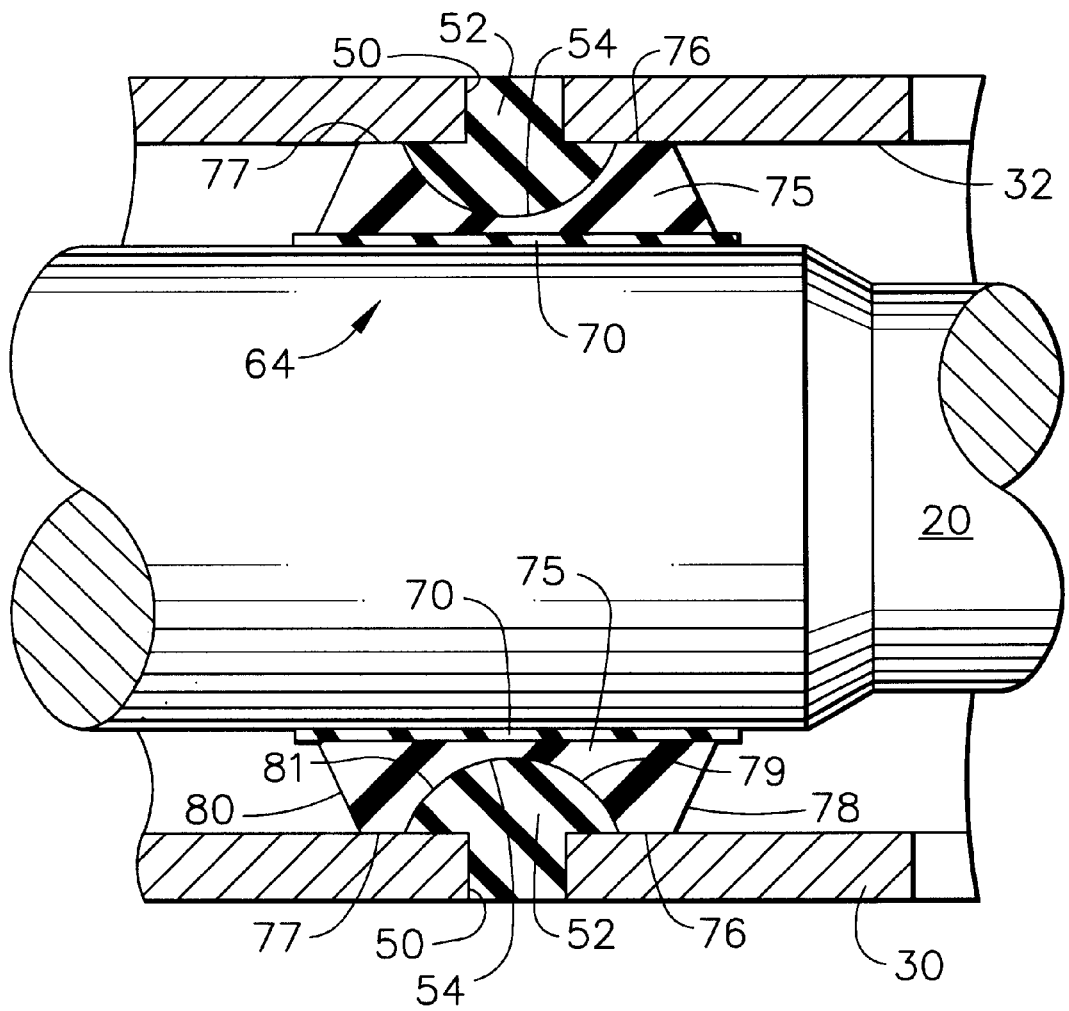
FIG. 7 is a magnified cutaway view of the seal region of the distal end of the ultrasonic instrument illustrated in FIG. 2 including a primer layer between the seal and the ultrasonic waveguide.

FIG. 7 is a magnified cutaway view of the seal region of the distal end of the ultrasonic instrument 18 including a primer 70 between acoustic isolation element 75 and ultrasonic waveguide 20. Bond strength of sealant 52 or acoustic isolation element 75 to inner surface 32 or waveguide 20 may be improved through the use of a primer material 70 as is known in the art. In FIG. 7, primer 70 is applied by spraying or painting primer material onto waveguide 20 before molding of acoustic isolation element 75 onto waveguide 20. For example, Dow Silicone primer 3-6060 may be applied to waveguide 20 prior to molding acoustic isolation element 75 comprising Dow Silicone 7-6860.

Ultrasonic acoustic isolation element 75 has been particularly configured and arranged, in conjunction with sealant 52, to form acoustic isolation seal 64. Acoustic isolation seal 64 facilitates sterilization of ultrasonic instrument 18 by providing a seal which is substantially impervious to liquids or gasses when the instrument is sterilized by, for example, soaking or steam autoclaving. Thus, utilizing an acoustic isolation seal according to the present invention, ultrasonic instrument 18 may be sterilized and reused without disassembly. Acoustic isolation seal 64 has a number of functions including: acting to acoustically isolate the active waveguide 20 from outer sheath 30; providing damping of undesired vibrations; as well as improving the seal between ultrasonic waveguide 20 and outer sheath 30. In particular, acoustic isolation seal 64 seals the distal end of ultrasonic instrument 18, substantially improving its ability to reduce or eliminate penetration by liquids or other contaminants during, for example, soaking or steam autoclave sterilization.

In an ultrasonic instrument according to the present invention, acoustic isolation seal 64 is preferably positioned at the distal-most node of ultrasonic waveguide 20 although such acoustic isolation seals may be positioned at any node along ultrasonic waveguide 20 or at more than one node. Positioning acoustic isolation seal 64 at the node nearest the end-effector is desirable to prevent tissue, blood, and other material from accumulating between waveguide 20 and outer sheath 30 distal to acoustic isolation seal 64. It is further advantageous to position acoustic isolation seal 64 such that acoustic isolation seal 64 is generally centered with respect to the vibratory node on which it is positioned.

Acoustic isolation seal 64 may be bonded to waveguide 20 by, for example, insert molding acoustic isolation element 75 to ultrasonic waveguide 20, creating a bond between acoustic isolation element 75 and ultrasonic waveguide 20. Acoustic isolation seal 64 is bonded to inner surface 32 of outer sheath 30 by sealant 52 which bonds acoustic isolation element 75 to outer sheath 30. This double bond reduces the need for compression to achieve a complete seal thus improving the ability of acoustic isolation element 75 to seal waveguide 20 to nonactive element 30.

A good bond, as opposed to a compression fit, of acoustic isolation seal 64 to ultrasonic waveguide 20 and outer sheath 30 is important to the success of the present invention. A good bond consists of an attachment between two elements, (for example; the ultrasonic waveguide 20 to acoustic isolation seal 75, or the acoustic isolation seal 75 to the inner surface 32 of outer sheath 30) wherein surface imperfections of one element are substantially filled by the second element, substantially locking the two elements together. A bond may be achieved by molding or curing the second element onto the first element. Alternatively, an adhesive may be used to fix the second element onto the first element, creating the bond. As is known, a primer may be used to provide a gripping surface for the second element to use as an attachment onto the first element.

A compression fit consists of a fit wherein peaks of surface imperfections on a first element suspending the second element above the valleys of the surface imperfections on the first element, thereby limiting intimate contact and attachment between the two surfaces. A compression fit is normally achieved by pre-forming or pre-molding the second element, and then shrinking it onto the first element. Alternatively, a compression fit may be achieved by mechanically or chemically expanding the second element, and then allowing it to contract onto the first element.

More particularly, an ultrasonic instrument according to the present invention may be manufactured by using the following procedure:

1—Prepare ultrasonic waveguide 20 for bonding to acoustic isolation element by cleaning and priming. For example the ultrasonic waveguide 20 may be wiped clean with Isopropyl Alcohol and primed with Dow Silicone primer 3-6060, and then allowed to dry.

2—Insert ultrasonic waveguide 20 into an injection molder. Molding acoustic isolation element 75, comprising, for example, Dow Silicone 7-6860 or VITON onto ultrasonic waveguide 20, thus bonding acoustic isolation element 75 to ultrasonic waveguide 20.

3—Place O-ring 25 over ultrasonic waveguide 20 until it rests against waveguide shoulder 27.

4—Insert ultrasonic waveguide 20 with acoustic isolation element 75 and O-ring 25 into outer sheath 30. Compressing O-ring 25 between waveguide shoulder 27 of ultrasonic waveguide 20 and mounting shoulder 37 of outer sheath 30.

5—Insert connector Pin 35 through sheath pin hole 23 of attachment hub 40 and waveguide pin hole 24 of waveguide 20. Connector pin 35 is retained in place by, for example, an interference fit or other means well known in the art.

6—Place the assembled ultrasonic instrument into a second injection molder and inject sealant 52 which may comprise, for example, Silicone or VITON through first injection opening 49 until all of the air is forced out of second injection opening 50 of outer sheath 30, filling annular recess 53, and bonding acoustic isolation element 75 to outer sheath 30.

It will be apparent that ultrasonic instruments including the present invention may be used in ultrasonic instruments adapted for open, laparoscopic or endoscopic surgical procedures. It will further be apparent that ultrasonic instruments according to the present invention are particularly adapted for multiple patient use.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An ultrasonic surgical instrument comprising:

an outer sheath having a proximal end, a distal end and an inner surface;

an ultrasonic waveguide positioned within said outer sheath and having an end-effector extending from said distal end of said outer sheath; and an acoustic isolation seal wherein said acoustic isolation seal comprises an acoustic isolation element bonded to said ultrasonic waveguide and a sealant positioned between said acoustic isolation element and said inner surface wherein said sealant is bonded to said acoustic isolation element and said inner surface, wherein said acoustic isolation element includes a distal sealing ridge and a proximal sealing ridge defining an annular groove around said acoustic isolation seal, said sealant filling said annular groove.

2. An ultrasonic surgical instrument according to claim 1 wherein said outer sheath includes at least one injection opening positioned over said annular groove.

3. An ultrasonic surgical instrument according to claim 1 wherein said acoustic isolation element and said sealant comprise an elastomeric material.

4. An ultrasonic surgical instrument according to claim 3 wherein at least one of said acoustic isolation element or said sealant comprises a fluoroelastomer synthetic rubber.

5. An ultrasonic surgical instrument according to claim 3 wherein at least one of said acoustic isolation element or said sealant comprises silicone.

6. An ultrasonic surgical instrument according to claim 1 wherein said acoustic isolation seal is approximately positioned at a vibratory node of said ultrasonic waveguide.

7. An ultrasonic surgical instrument comprising:

an outer sheath having a proximal end, a distal end and an inner surface;

an ultrasonic waveguide positioned within said outer sheath and having an end-effector extending from said distal end of said outer sheath; and an acoustic isolation seal wherein said acoustic isolation seal is bonded to said ultrasonic waveguide and to said outer sheath interior surface, wherein said acoustic isolation seal includes a distal sealing ridge and a proximal sealing ridge defining an annular groove around said ultrasonic waveguide, a sealant filling said annular groove.

8. An ultrasonic surgical instrument according to claim 7 wherein said outer sheath includes at least one injection opening positioned over said annular groove.

9. An ultrasonic surgical instrument according to claim 7 wherein said acoustic isolation seal and said sealant comprises an elastomeric material.

10. An ultrasonic surgical instrument according to claim 9 wherein said acoustic isolation seal comprises a fluoroelastomer synthetic rubber.

11. An ultrasonic surgical instrument according to claim 9 wherein said acoustic isolation seal comprises silicone.

12. An ultrasonic surgical instrument according to claim 7 wherein said acoustic isolation seal is positioned at a node of said ultrasonic waveguide.

* * * * *